(12) United States Patent
Vunk et al.

(10) Patent No.: US 7,348,301 B2
(45) Date of Patent: Mar. 25, 2008

(54) LYSOZYME-BASED METHOD AND COMPOSITION TO CONTROL THE GROWTH OF MICROORGANISMS IN AQUEOUS SYSTEMS

(75) Inventors: Graciela H. Vunk, Olive Branch, MS (US); Deborah A. Marais, Lakeland, TN (US)

(73) Assignee: Buckman Laboratories International, Inc., Memphis, TN (US)

( * ) Notice: Subject to any disclaimer, the term of this patent is extended or adjusted under 35 U.S.C. 154(b) by 2 days.

(21) Appl. No.: 11/355,589

(22) Filed: Feb. 16, 2006

(65) Prior Publication Data

US 2007/0191255 A1 Aug. 16, 2007

(51) Int. Cl.
*C11D 3/386* (2006.01)
*C11D 3/48* (2006.01)
*C11D 1/62* (2006.01)

(52) U.S. Cl. ............... 510/247; 510/199; 510/254; 510/384; 510/392

(58) Field of Classification Search ........... 510/199, 510/247, 254, 384, 392
See application file for complete search history.

(56) References Cited

U.S. PATENT DOCUMENTS

| | | | |
|---|---|---|---|
| 3,874,870 A | 4/1975 | Green et al. | |
| 3,931,319 A | 1/1976 | Green et al. | |
| 4,027,020 A | 5/1977 | Green et al. | |
| 4,089,977 A | 5/1978 | Green et al. | |
| 4,111,679 A | 9/1978 | Shair et al. | |
| 4,506,081 A | 3/1985 | Fenyes et al. | |
| 4,581,058 A | 4/1986 | Fenyes et al. | |
| 4,778,813 A | 10/1988 | Fenyes et al. | |
| 4,970,211 A | 11/1990 | Fenyes et al. | |
| 5,051,124 A | 9/1991 | Pera | |
| 5,069,717 A * | 12/1991 | Sherba et al. ............ 106/18.35 |
| 5,093,078 A | 3/1992 | Hollis et al. | |
| 5,128,100 A | 7/1992 | Hollis et al. | |
| 5,142,002 A | 8/1992 | Metzner | |
| 5,200,182 A * | 4/1993 | Kiczka ................. 424/94.5 |
| 5,466,449 A * | 11/1995 | Kiczka ................. 424/94.61 |
| 6,123,937 A * | 9/2000 | Kiczka ................. 424/94.61 |
| 6,753,179 B2 * | 6/2004 | Tsuchiya ............... 435/262.5 |
| 6,825,157 B2 * | 11/2004 | Sivik et al. ............. 510/237 |
| 6,830,745 B1 * | 12/2004 | Budny et al. ............ 424/49 |
| 2004/0132095 A1 * | 7/2004 | Iizumi et al. ............ 435/7.1 |
| 2005/0014932 A1 * | 1/2005 | Imboden et al. .......... 530/350 |
| 2005/0049181 A1 * | 3/2005 | Madhyastha ............. 514/8 |
| 2005/0112251 A1 * | 5/2005 | Stark et al. ............. 426/330.3 |
| 2005/0242029 A1 * | 11/2005 | Sava .................. 210/632 |
| 2005/0266050 A1 * | 12/2005 | Smith et al. ............ 424/442 |

FOREIGN PATENT DOCUMENTS

JP 57-032226 2/1982

OTHER PUBLICATIONS

Mine et al., "Novel antibacterial peptides derived from hen egg lysozyme," 2002 Annual Meeting and Food Expo, Jun. 2002 (1 page).
Lesnierowski et al., "Antibacterial Activity of Thermally Modified Lysozyme," Electronic Journal of Polish Agricultural Universities, Food Science and Technology, vol. 4, Issue 2, 2001 (pp. 1-8).
Ibrahim et al., "Genetic Evidence That Antibacterial Activity of Lysozyme is Independent of its Catalytic Function," FEBS Letters, 506, 2001 (pp. 27-32).
Masschalck et al., "Inactivation of Gram-Negative Bacteria by Lysozyme, Denatured Lysozyme, and Lysozyme-Derived Peptides under High Hydrostatic Pressure," Applied and Environmental Microbiology, vol. 67, No. 1, Jan. 2001 (pp. 339-344) (12 pages).

* cited by examiner

*Primary Examiner*—Charles Boyer
(74) *Attorney, Agent, or Firm*—Kilyk & Bowersox, P.L.L.C.

(57) ABSTRACT

A method for killing, preventing, or inhibiting the growth of microorganisms in an aqueous system or on a substrate capable of supporting a growth of microorganisms is provided by providing lysozyme, alone or in combination with a quaternary ammonium compound to the aqueous system or substrate.

21 Claims, No Drawings

LYSOZYME-BASED METHOD AND COMPOSITION TO CONTROL THE GROWTH OF MICROORGANISMS IN AQUEOUS SYSTEMS

FIELD OF THE INVENTION

The present invention relates to compositions and methods to control the growth of microorganisms in aqueous systems. More particularly, the present invention relates to the treatment of aqueous systems with lysozyme alone or in combination with quaternary ammonium compounds.

BACKGROUND OF THE INVENTION

A variety of materials have been used to control algae in different environments, such as but not exclusive to: chlorine/bromine based compounds, biguanides, copper salts, silver-based compounds, triazines, quaternary ammonium compounds and polymeric compounds. Each of them has deficiencies related to pH and/or temperature sensitivity, chemical stability and/or compatibility, limited effectiveness, and environmental and/or human toxicity.

For example, chlorine is the sanitizer/disinfectant/oxidizer most widely used by pool owners. It is very effective at killing bacteria, algae and other living organisms. Chlorine is typically added to a swimming pool in tablet or liquid form or is provided by a chlorine generator, which is a device containing electrical cells that generate chlorine from a bank of salt added to the pool water.

However, chlorine has many disadvantages that lessen its desirability for use as an exclusive disinfectant in swimming pools and other recreational water systems. For example, chlorine can combine with ammonia to form chloramines, which are ineffective at sanitizing, disinfecting, or oxidizing. Ammonia is commonly present in pool water from either environmental factors, a build up of fertilizers that are carried by wind and dropped into pools, from swimmer wastes (perspiration, urine, saliva and body oils), or even from some suntan lotions. As a consequence, pool managers often over-chlorinate a pool (>3 ppm) to compensate for the transformation of chlorine into chloramines. Over-chlorination can lead to excessive absorption of chlorine and chloramines through the skin or to inhalation of air or water vapor containing chlorine and chloramines. Athletes who train for many hours in a swimming pool, particularly in an indoor environment, may be particularly susceptible to over-exposure to chlorine and chloramines and may exhibit symptoms of hypersensitivity and asthma-like respiratory conditions.

Moreover, chlorine is unsuitable for aquaculture environments that may contain desirable plants and animals that may be harmed by chlorine or its byproducts. Examples of such environments include aquariums, fish hatcheries, shrimp ponds, crawfish farms, and the like.

Lysozyme is known as a powerful antibacterial protein distributed in various biological fluids and tissues including avian egg, plant, bacteria, and animal secretions. It is also present in human tears, saliva, milk, respiratory and cervical secretions, and it is secreted by polymorphonuclear leukocytes. Lysozyme has been used for its antibacterial properties both in the pharmaceutical and food industries and been regarded as very safe for human use. In fact, lysozyme is one of the antimicrobial factors present in human milk.

U.S. Pat. No. 5,069,717 to Sherba et al. describes microbicidal composition for controlling algae containing synergistic mixture of a diphenylether and lysozyme.

Accordingly, it is desirable to have a method of preventing, killing, and/or inhibiting the growth of microorganisms that is inexpensive and uses an ingredient that is effective at a low concentration and that is easily available.

It is also desirable to have a method of preventing, killing, and/or inhibiting the growth of microorganisms that does not use chlorine or other environmentally undesirable ingredients.

SUMMARY OF THE INVENTION

It has now been found that a potent antimicrobial composition to control growth of microorganisms, particularly algae, in aqueous systems may be obtained by providing lysozyme, either alone or in combination with at least one quaternary compound to the aqueous system. The present invention can be applied in a variety of industrial fluid systems (e.g., aqueous systems) and processes, including but not limited to, paper-making water systems, pulp slurries, white water in paper-making process, cooling water systems (cooling towers, intake cooling waters and effluent cooling waters), waste water systems, recirculating water systems, hot tubs, swimming pools, recreational water systems, food processing systems, drinking water systems, leather-processing water systems, metal working fluids, and other industrial water systems.

In one embodiment of the present invention, lysozyme can be added to a saline water system, such as, but not exclusively, a water system using a saline chlorination system. The lysozyme can optionally act synergistically with sodium chloride to provide a composition to control growth of microorganisms, particularly, for example, algae.

Additional features and advantages of the present invention will be set forth in part in the description that follows, and in part will be apparent from the description, or may be learned by practice of the present invention. The objectives and other advantages of the present invention will be realized and attained by means of the elements and combinations particularly pointed out in the description and appended claims.

It is to be understood that both the foregoing general description and the following detailed description are exemplary only and are not restrictive of the present invention, as claimed. All patents, patent applications, and publications mentioned above and throughout the present application are incorporated in their entirety by reference herein.

DETAILED DESCRIPTION OF THE PRESENT INVENTION

The present invention provides methods and compositions for controlling the growth of microorganisms, in aqueous systems using lysozyme, alone or in combination with at least one quaternary ammonium compound.

According to the methods of the present invention, controlling or inhibiting the growth of at least one microorganism includes the reduction and/or the prevention of such growth.

As used herein, the term "aqueous system" includes recreational water systems, particularly recirculating water systems such as hot tubs, spas and swimming pools and industrial fluid systems, including but not limited to, paper-making water systems, pulp slurries, white water in paper-making process, cooling water systems (cooling towers, intake cooling waters and effluent cooling waters), waste water systems, food processing systems, drinking water systems, leather-processing water systems, metal working fluids, and other industrial water systems.

The present invention is particularly suitable for aqueous water systems that come into contact with higher organisms, which are not harmed by lysozyme because of its low toxicity. Therefore, the present invention may be used, for example, for controlling microorganisms, e.g., algae, in swimming pools, spas and hot tubs and for controlling algae in water systems used in aquaculture, including fish hatcheries, fish farms, shrimp ponds, crawfish ponds, mollusk, and the like.

As an example, lysozyme can be added to a saline water system, such as a water system using a saline chlorination system. For example, the water system may contain from about 2,000 ppm to about 8,000 ppm, such as 2,800 ppm to 6,000 ppm, of sodium chloride. The lysozyme can optionally act synergistically with sodium chloride to provide a composition to control the growth of microorganisms, particularly algae. Because of the activity of lysozyme to control algae and/or other microorganisms, there may be a reduced need to run the chlorine generator in such a water system, thereby reducing electrical costs and reducing the likelihood of undesirable effects from over-chlorination.

Lysozyme may also be added to control algae and other microorganisms in an aqueous systems that has been treated for reduction or removal of chlorine. For example, aquariums may contain plant and animal species that are sensitive to chlorine, even in the amount that is present in common municipal water sources, so that the water used therein must be filtered or treated for the removal of chlorine. Lysozyme can then supply at least some of the microorganism-controlling activity that is lost by the reduction or removal of chlorine.

It is to be further understood that by "controlling" (e.g., preventing) the growth of at least one microorganism, the growth of the microorganism is at least partially inhibited. In other words, there is no growth or essentially no growth of the microorganism. "Controlling" the growth of at least one microorganism maintains the microorganism population at a desired level, reduces the population to a desired level (even to undetectable limits), and/or at least partially inhibits the growth of the microorganism. Thus, in one embodiment of the present invention, the products, material, or media susceptible to attack by the at least one microorganism are at least partially preserved from this attack and the resulting spoilage and other detrimental effects caused by the microorganism. Further, it is also to be understood that "controlling" the growth of at least one microorganism also includes biostatically reducing and/or maintaining a low level of at least one microorganism such that the attack by the microorganism and any resulting spoilage or other detrimental effects are mitigated, i.e., the microorganism growth rate or microorganism attack rate is slowed down and/or eliminated. The compositions of the present invention preferably have a low toxicity.

Examples of these microorganisms include fungi, bacteria, algae, and mixtures thereof, such as, but not limited to, for example, *Trichoderma viride, Aspergillus niger*, and *Chlorella* sp. A further example is a gram-positive microorganism, like *Bacillus* species.

Lysozyme is typically designated in enzyme nomenclature as "EC 3.2.1.17 and is also commonly called muramidase. The lysozyme used in the present invention may come from any known source of lysozyme, such as from any plant or animal source and may be obtained by any method of enzyme production, isolation, or purification, including recombinant means. Lysozyme is commercially available in purified form on an industrial scale. Typically, the purified enzyme comes in the form of a white solid.

As an option, the lysozyme can be a heat-treated lysozyme or a thermally-modified lysozyme. The lysozyme can be a lysozyme dimer. The lysozyme can be thermally-modified, for instance, by heating the lysozyme at an elevated temperature, such as heating in a water bath. The temperature can be any temperature sufficient to modify the lysozyme, for instance, to form a lysozyme dimer. For instance, a temperature of about 50° C. or higher can be used, such as 70° C. to 100° C., more particularly, a temperature of 80° C., for about 20 minutes. For purposes of the present invention, more than one type of lysozyme can be present. For instance, one unmodified lysozyme can be present with a thermally-modified lysozyme. Furthermore, the lysozyme dimer can have other lysozymes present. For instance, the lysozyme of the present invention can have 5% lysozyme dimer present to 50% lysozyme dimer present or more. For instance, the lysozyme dimer can be present in an amount of from 1% to 50% or 10% to 35%. The heat-treated or thermally-modified lysozyme can act as a partial or complete heat denaturation of the lysozyme. As stated, any combination of the lysozymes can be used in the present invention.

As described herein, the optional addition or presence of at least one quaternary ammonium compound further enhances the antimicrobial activity when used with lysozyme, and particularly enhances the antialgal activity. For example, quaternary ammonium compounds such as alkyl dimethyl benzyl ammonium chloride are commercially available as algaecides. The use of a quaternary ammonium compound may provide a broader spectrum of antialgal activity or may provide increased efficacy against problematic algae. In particular, it is believed that lysozyme and a quaternary ammonium compound act synergistically to provide a particularly useful and economical antimicrobial system.

The quaternary ammonium compound that may be used to provide additional synergistic antimicrobial effects according to the present invention may be obtained from any ammonium source. For example, the quaternary ammonium compound may be may be a compound with a single quaternary ammonium group or a polyquaternary ammonium compound. Examples of suitable quaternary ammonium compounds include for example, N,N-diethyl-N-dodecyl-N-benzylammonium chloride, N,N-dimethyl-N-octadecyl-N-(dimethylbenzyl)ammonium chloride, N,N-dimethyl-N,N-didecylammonium chloride, N,N-dimethyl-N,N-didodecylammonium chloride, N,N,N-trimethyl-N-tetradecylammonium chloride, N-benzyl-N,N-dimethyl-N—($C_{12}$-$C_{18}$ alkyl) ammonium chloride, N-(dichlorobenzyl)-N,-N-dimethyl-N-dodecylammonium chloride, N-hexadecylpyridinium chloride, N-hexadecylpyridinium bromide, N-hexadecyl-N,N,N-trimethylammonium bromide, N-dodecylpyridinium chloride, N-dodecylpyridinium bisulphate, N-benzyl-N-dodecyl-N,N-bis(beta-hydroxy-ethyl)ammonium chloride, N-dodecyl-N-benzyl-N,N-dimethylammonium chloride, N-benzyl-N,N-dimethyl-N—($C_{12}$-$C_{18}$ alkyl) ammonium chloride, N-dodecyl-N,N-dimethyl-N-ethylammonium ethylsulfate, N-dodecyl-N,N-dimethyl-N-(1-naphthylmethyl) ammonium chloride, N-hexadecyl-N,N-dimethyl-N-benzylammonium chloride or N-dodecyl-N,N-dimethyl-N-benzylammonium chloride. The quaternary ammonium compound may also be a polyquaternary ammonium compound. Antimicrobial polyquaternary ammonium compounds which may be used include those described in U.S. Pat. Nos. 3,874,870, 3,931,319, 4,027,020, 4,089,977, 4,111,679, 4,506,081, 4,581,058, 4,778,813, 4,970,211, 5,051,124, 5,093,078, 5,142,002 and 5,128,100 which are incorporated herein by reference thereto. An example of a polyquaternary ammonium compound is poly(oxyethylene-(dimethyliminio)ethylene (dimethyliminio)ethylenedichloride), which is commercially available under the Trademark WSCP from Buckman Laboratories International, Inc.

As a method of killing, or preventing, or inhibiting the growth of microorganisms in an aqueous system, the lysozyme and, optionally, the quaternary ammonium compound, may be provided to the aqueous system under conditions wherein the lysozyme and quaternary ammonium compound act to provide an antimicrobial agent that kills, or prevents, or inhibits the growth of microorganisms in the aqueous system.

One of ordinary skill can readily determine the effective amount of lysozyme and optional quaternary ammonium compound useful for a particular application by simply testing various concentrations prior to treatment of an entire affected system. For instance, in an aqueous system to be treated, the concentration of lysozyme may be any effective amount, such as from about 0.01 ppm to 5,000 ppm, and when treating algae, a preferred range is from about 0.01 ppm to about 2,000 ppm, and is preferably in a range of from about 0.1 to about 500 ppm.

The quaternary ammonium compound may be present in the aqueous system in any effective amount, such as in a range of from 0.01 ppm to about 1,000 ppm and preferably in the range of about 0.1 ppm to about 100 ppm.

The concentrations of lysozyme and quaternary ammonium compound as described above or as described elsewhere in this application, may be the initial concentrations of the components at the time that the components are combined or added to an aqueous system and/or may be the concentrations of the components at any time after the components have interacted with the aqueous system.

If both lysozyme and at least one quaternary ammonium compound are used in the method of the present invention, the ingredients may be added separately to an aqueous system or they may be combined to form a composition that is added to the aqueous system. If they are added separately, the order of component addition is not critical and any order can be used.

The method of the present invention may be practiced at any pH, such as a pH range of from about 2 to about 11, with a preferable pH range of from about 5 to about 9. For an aqueous system that will be in contact with higher organisms, such as humans or fish, the pH should be neutral (around pH 7). The pH of the aqueous system may be adjusted by adding an acid(s) or a base(s) as is known in the art. The acid or base added should be selected to not react with any components in the system. However, it is preferable to add the lysozyme and optional quaternary ammonium compound to water without pH adjustment.

The method of the present invention may be used in any industrial or recreational aqueous systems requiring microorganism control. Such aqueous systems include, but are not limited to, metal working fluids, cooling water systems (cooling towers, intake cooling waters and effluent cooling waters), waste water systems including waste waters or sanitation waters undergoing treatment of the waste in the water, e.g. sewage treatment, recirculating water systems, swimming pools, hot tubs, food processing systems, drinking water systems, leather-processing water systems, white water systems, pulp slurries and other paper-making or paper-processing water systems. In general, any industrial or recreational water system can benefit from the present invention. The method of the present invention may also be used in the treatment of intake water for such various industrial processes or recreational facilities. Intake water can be first treated by the method of the present invention so that the microbial growth is inhibited before the intake water enters the industrial process or recreational facility.

The present invention will be further clarified by the following examples, which are intended to be exemplary of the present invention.

EXAMPLES

General Procedures

A. Evaluation of Algaecidal Activity. This test method provides a technique for testing compounds for their effectiveness to inhibit (repress) algae growth. MIC values represents the Minimum Inhibitory Concentration, defined as the lowest level of compound required to completely inhibit (repress) the growth of a given organism.

Apparatus:
  Test tubes, 18-150 mm. Sterilized test tubes are required.
  Incubator, capable of a constant (±2° C.) temperature and light regulation.

Reagents and Materials:
  $KNO_3$
  $K_2HPO_4$
  $MgSO_4.7H_2O$
  Fe-ammonium citrate (1% solution)

Stock solutions:

| | Stock solution component | g/200 g deionized water |
|---|---|---|
| A. | $K_2HPO_4$ | 1.50 |
| B. | $MgSO_4•7H_2O$ | 1.50 |
| C. | $Na_2CO_3$ | 0.80 |
| D. | $CaCl_2•2H_2O$ | 0.50 |
| E. | $Na_2SiO_3•9H_2O$ | 1.16 |
| F. | Citric acid | 1.20 |
| G. | PIV metals | |
| | $Na_2$ EDTA | 0.750 g |
| | $FeCl_3•6H_2O$ | 0.097 g |
| | $MnCl_2•4H_2O$ | 0.041 g |
| | $ZnCl_2$ | 0.005 g |
| | $CoCl_2•6H_2O$ | 0.002 g |
| | $Na_2MoO_4•2H_2O$ | 0.004 g |
| | Deionized water | 1,000.000 ml |

Inoculum.
  Cell suspension from a culture grown in modified Allen's medium for 14 days or as needed to attain a desired cell mass of *Chlorella* sp. (ATCC 7516) or *Phormidium faveolarum* (UTEX 427). The inoculum is calibrated at 82% transmittance measured at 590 nanometers wavelength before inoculation.

Procedure:

Medium preparation:
Modified Allen's medium (Allen, A. A., 1968).

| | |
|---|---|
| $NaNO_3$ | 1.5 g |
| $K_2HPO_4$ | 5.0 ml stock solution A. |
| $MgSO_4•7H_2O$ | 5.0 ml stock solution B. |

-continued

| | |
|---|---|
| Na$_2$CO$_3$ | 5.0 ml stock solution C. |
| CaCl$_2$·2H$_2$O | 10.0 ml stock solution D. |
| Na$_2$SiO$_3$·9H$_2$O | 10.0 ml stock solution E. |
| Citric acid | 1.0 ml stock solution F. |
| PIV metal | 1.0 ml stock solution G. |
| Deionized water | 1000.0 ml. |

Sterilize the medium in the autoclave for 20 minutes at 15 pounds pressure (121° C.). After autoclaving, cool medium to 45-50° C. and dispense 5 ml of medium per test tube, then add the compound and the inoculum.

Compound Incorporation:

Prepare a stock solution in water of the compound to be tested. The concentration of the stock solution is dependent on the largest dosage desired to be tested. Dilute the stock solution to obtain dosages smaller than that chosen for the stock solution. A maximum amount of 100 microliters of stock solution or the corresponding dilution should be added per test tube.

Inoculation:

Add 100 microliters of inoculum per test tube, per type of medium and type of inoculum.

Incubation:

Place the test tubes containing the treatments in an incubator set at 24° C. Light is provided by plant growth fluorescent tubes set to provide 16 h of light and 8 h of darkness.

Rating of the Tubes:

The test tubes with the treatments are rated positive or negative:

Positive (contaminated) when the medium in the tubes shows algae growth (green deposit at the bottom).

Negative (not contaminated) when the medium in the tubes remains colorless.

The control is always positive. The minimum inhibitory concentration (MIC) of the compound is the smallest dosage showing negative algae growth.

Synergy Evaluation:

Synergy was measured by checkerboards dilutions (Yan and Hancock, 2001), in which one compound is diluted along the rows of test tubes and the other is diluted along the columns. This method focuses on looking for a reduction in the MIC of each component in the presence of the other. The result is expressed as the Fractional Inhibitory Concentration Index (FIC), calculated as follows:

FIC=[$A$]/MIC$_A$+[$B$]/MIC$_B$ where,

MIC$_A$ and MIC$_B$=MICs of the compounds A and B alone
[A] and [B]=MICs of the compounds A and B when in combination An FIC index<1 indicates synergy; an index of 0.5 represents the equivalent of a fourfold decrease in the MIC of each compound in combination. An FIC index of 1.0 represents additive activity (a twofold decrease in the MIC of each compound in combination), and an index>1 indicates antagonism; an index>4 represents true antagonism.

B. Evaluation of Bactericidal Activity. This method is suitable for use in evaluating the antibacterial properties of chemicals by determining their MIC value. The MIC value represents the Minimum Inhibitory Concentration defined as the lowest level of compound required to achieve a >90% kill of a given organism.

Equipment:
1. Test tubes, 18×150 mm disposable culture tubes—sterile
2. Sterile 1 ml and 10 ml pipettes
3. Incubator capable of maintaining a temperature of 37° C.±1° C.
4. Autoclave
5. pH meter
6. 1-200 ul micropipette tips
7. Eppendorf Micropipette
8. McFarland Standard #1
9. Petri Dishes: Plastic disposable Petri-dishes, 100×15 mm size 3. Media Preparation:

1. Difco Plate Count Agar: Rehydrate the agar by suspending 23.5 g in 1-L of deionized water and heat to boiling to dissolve. Dispense as desired and sterilize in a steam autoclave for 15 minutes at 121° C.
2. Basal Salts Substrate, pH7:

| | |
|---|---|
| Trizma ® (Tris) HCl | 3.9 g |
| Trizma ® (Tris) Base. | 0.05 g |

(Note: Obtain proper pH before addition of the following. Adjust with either more of the appropriate Trizma ® buffer)

| | |
|---|---|
| Glucose | 0.02 grams |
| Peptone | 0.01 grams |
| Ammonium nitrate | 1.0 grams |
| Magnesium sulfate, heptahydrate | 0.25 grams |
| Calcium Chloride | 0.25 grams |

Autoclave at 121° C. for 15 minutes

C. Inoculum. Cell suspension from an 18 to 24 hour bacterial culture of *Staphylococcus aureus* (ATCC 6538) or *Bacillus subtilis* (ATCC 6633) or *Enterobacter aerogenes* (ATCC 13048) to attain a desired cell concentration. Using a McFarland nephelometer barium sulfate standard or some other suitable method, adjust the concentration of the bacterial suspension so that a final concentration of between $1\times10^4$ and $1\times10^5$ cells per ml is achieved when 100 µl of the inoculum is added to 5 ml of basal salts substrate.

D. Compound Incorporation. Prepare a stock solution in water of the compound to be tested. The concentration of the stock solution is dependent on the largest dosage desired to be tested. Dilute the stock solution to obtain dosages smaller than that chosen for the stock solution. A maximum amount of 100 µl of stock solution or the corresponding dilution should be added per test tube.

E. Inoculation and incubation. Add 100 µl of inoculum per test tube per type of medium and type of inoculum, and incubate at 37° C. for 18 hours.

F. Rating of tubes via plate count method. The Pour Plate Count agar was prepared as described in *Standard Methods* (American Public Health Association; 1995). One milliliter of the sample was placed on the center of a sterile petri dish (100-mm diameter) by using a sterile pipette. Sterile, molten (44 to 46° C.) plate count agar (pH 7.0; Difco) was added and mixed with the sample by swirling the plate. The samples were allowed to cool at room temperature until solidified and then were inverted and incubated at 35±0.5° C. for 48±2 h. Colonies formed in or on the plate count medium within 48±2 h were counted as described in *Standard Methods*, and the results were reported as CFU/milliliter. Where applicable, this value was multiplied by the dilution factor to obtain the corrected CFU/milliliter.

In this test, the MIC of the compound is the concentration that produced 90% kill. This is calculated using the following equation:

$$\frac{\text{Average } CFU/\text{ml in controls} - \text{Average } CFU/\text{ml in treatment}}{\text{Average } CFU/\text{ml in controls}} \times 100$$

G. Synergy Evaluation. Synergy was measured by checkerboards dilutions (Yan and Hancock, 2001), in which one compound is diluted along the rows of test tubes and the other is diluted along the columns. This method focuses on looking for a reduction in the MIC of each component in the presence of the other. The result is expressed as the Fractional Inhibitory Concentration Index (FIC), calculated as follows:

FIC=[A]/MIC$_A$+[B]/MIC$_B$ where,

MIC$_A$ and MIC$_B$=MICs of the compounds A and B alone

[A] and [B]=MICs of the compounds A and B when in combination

An FIC index<1 indicates synergy; an index of 0.5 represents the equivalent of a fourfold decrease in the MIC of each compound in combination. An FIC index of 1.0 represents additive activity (a twofold decrease in the MIC of each compound in combination), and an index>1 indicates antagonism; an index>4 represents true antagonism.

This is a purely enzymatic system for controlling algae. Lysozyme is preferably used by itself as the active ingredient in this invention.

Lysozyme (Sigma), Lysozyme Chloride (NutriScience), Lysozyme Chloride (MP Biomedicals) were tested against *Chlorella* sp. (ATCC 7516). The incubation period was 14 days at 24 C under 16 h of light and 8 h of darkness.

| Enzyme | MIC (ppm product) |
| --- | --- |
| Lysozyme (Sigma) | 0.4-0.7 |
| Lysozyme Chloride (NutriScience) | 0.4-0.7 |
| Lysozyme Chloride (MP Biomedicals) | 0.1-0.4 |

Lysozyme can also be applied in combination with quaternary ammonium compounds commonly used in the water treatment and recreational water industries (e.g. BUSAN 77™ product) to control algae.

Example 1

Combinations of Lysozyme chloride (MP Biomedicals) with Benzalkonium Chloride. The organism tested was *Chlorella* sp. (ATCC 7516). The incubation period was 18 days at 24 C under 16 h of light and 8 h of darkness.

| Lysozyme [A] | Benzalkonium Chloride [B] | [A]/MIC$_A$ | [B]/MIC$_B$ | [A]/MIC$_A$ + [B]/MIC$_B$ |
| --- | --- | --- | --- | --- |
| 0 | 2 MIC$_B$ | 0.000 | 1.000 | 1.000 |
| 0.1 | 1 | 0.050 | 0.500 | 0.550 |
| 0.4 | 1 | 0.200 | 0.500 | 0.700 |
| 0.7 | 0.4 | 0.350 | 0.200 | 0.550* |
| 1 | 0.1 | 0.500 | 0.050 | 0.550 |
| 2 MIC$_A$ | 0 | 1.000 | 0.000 | 1.000 |

MIC$_A$ = MIC of Lysozyme Chloride alone = 2.00 mg product/l
MIC$_B$ = MIC of Benzalkonium Chloride alone = 2.00 mg product/l
[A] = MIC of Lysozyme Chloride in combination with Benzalkonium Chloride (mg product/l)
[B] = MIC of Benzalkonium Chloride in combination with Lysozyme Chloride (mg a.i./l)
*= A value <1 denotes synergistic activity of both components used simultaneously.

Example 2

Combinations of Lysozyme chloride (MP Biomedicals) with Benzalkonium Chloride. The organism tested was *Phormidium faveolarum* (UTEX 427). The incubation period was 18 days at 24 C under 16 h of light and 8 h of darkness.

| Lysozyme [A] | Benzalkonium Chloride [B] | [A]/MIC$_A$ | [B]/MIC$_B$ | [A]/MIC$_A$ + [B]/MIC$_B$ |
| --- | --- | --- | --- | --- |
| 0 | 2 MIC$_B$ | 0.0 | 1.0 | 1.00 |
| 0.1 | 1 | 0.1 | 0.50 | 1.50 |
| 0.4 | 1 | 0.4 | 0.50 | 0.90* |
| 0.7 | 0.7 | 0.7 | 0.35 | 1.05 |
| 1 MIC$_A$ | 0 | 1.0 | 0.00 | 1.00 |

MIC$_A$ = MIC of Lysozyme Chloride alone = 1.00 mg product/l
MIC$_B$ = MIC of Benzalkonium Chloride alone = 2.00 mg product/l
[A] = MIC of Lysozyme Chloride in combination with Benzalkonium Chloride (mg product/l)
[B] = MIC of Benzalkonium Chloride in combination with Lysozyme Chloride (mg a.i./l)
*= A value <1 denotes synergistic activity of both components used simultaneously.

Example 3

Combinations of Lysozyme chloride (MP Biomedicals) with BUSAN 77™ product. The organism tested was *Chlorella* sp. (ATCC 7516). The incubation period was 18 days at 24 C under 16 h of light and 8 h of darkness.

| Lysozyme [A] | BUSAN 77™ product [B] | [A]/MIC$_A$ | [B]/MIC$_B$ | [A]/MIC$_A$ + [B]/MIC$_B$ |
| --- | --- | --- | --- | --- |
| 0 | 0.7 MIC$_B$ | 0.000 | 1.000 | 1.000 |
| 0.01 | 0.7 | 0.005 | 1.000 | 1.005 |
| 0.04 | 0.7 | 0.020 | 1.000 | 1.020 |
| 0.07 | 0.7 | 0.035 | 1.000 | 1.385 |
| 0.1 | 0.4 | 0.050 | 0.571 | 0.621* |
| 0.4 | 0.04 | 0.200 | 0.057 | 0.257 |
| 0.7 | 0.04 | 0.350 | 0.057 | 0.407 |
| 1 | 0.01 | 0.500 | 0.014 | 0.514 |
| 2 MIC$_A$ | 0 | 1.000 | 0.000 | 1.000 |

MIC$_A$ = MIC of Lysozyme Chloride alone = 2.00 mg product/l
MIC$_B$ = MIC of BUSAN 77™ product alone = 0.7 mg product/l
[A] = MIC of Lysozyme Chloride in combination with BUSAN 77™ product (mg product/l)
[B] = MIC of BUSAN 77™ product in combination with Lysozyme Chloride (mg a.i./l)
*= A value <1 denotes synergistic activity of both components used simultaneously.

Example 4

Combinations of Lysozyme chloride (MP Biomedicals) with BUSAN 77™ product. The organism tested was *Phormidium faveolarum* (UTEX 427). The incubation period was 18 days at 24 C under 16 h of light and 8 h of darkness.

| Lysozyme [A] | BUSAN 77™ product [B] | $[A]/MIC_A$ | $[B]/MIC_B$ | $[A]/MIC_A$ + $[B]/MIC_B$ |
|---|---|---|---|---|
| 0 | 2 $MIC_B$ | 0.00 | 1.000 | 1.000 |
| 0.01 | 2 | 0.01 | 1.000 | 1.010 |
| 0.04 | 2 | 0.04 | 1.000 | 1.040 |
| 0.07 | 2 | 0.07 | 1.000 | 1.070 |
| 0.1 | 0.7 | 0.10 | 0.350 | 0.450* |
| 0.4 | 0.4 | 0.40 | 0.200 | 0.600 |
| 0.7 | 0.01 | 0.70 | 0.005 | 0.705 |
| 1 $MIC_A$ | 0 | 1.00 | 0.000 | 1.000 |

$MIC_A$ = MIC of Lysozyme Chloride alone = 1.00 mg product/l
$MIC_B$ = MIC of BUSAN 77 ™ product alone = 2.00 mg product/l
[A] = MIC of Lysozyme Chloride in combination with BUSAN 77 ™ product (mg product/l)
[B] = MIC of BUSAN 77 ™ product in combination with Lysozyme Chloride (mg a.i./l)
*= A value <1 denotes synergistic activity of both components used simultaneously.

Example 5

Combinations of Lysozyme chloride (MP Biomedicals) with BUSAN 77™ product. The organism tested was *Chlorella* sp. (ATCC 7516). The incubation period was 34 days at 24 C under 16 h of light and 8 h of darkness.

| Lysozyme [A] | BUSAN 77™ product [B] | $[A]/MIC_A$ | $[B]/MIC_B$ | $[A]/MIC_A$ + $[B]/MIC_B$ |
|---|---|---|---|---|
| 0 | 2 $MIC_B$ | 0.000 | 1.000 | 1.000 |
| 0.01 | 2 | 0.005 | 1.000 | 1.005 |
| 0.04 | 2 | 0.020 | 1.000 | 1.020 |
| 0.07 | 0.7 | 0.035 | 0.350 | 0.385* |
| 0.1 | 0.7 | 0.050 | 0.350 | 0.400 |
| 0.4 | 0.1 | 0.080 | 0.050 | 0.130 |
| 0.7 | 0.1 | 0.350 | 0.050 | 0.400 |
| 1 | 0.1 | 0.500 | 0.050 | 0.550 |
| 2 $MIC_A$ | 0 | 1.000 | 0.000 | 1.000 |

$MIC_A$ = MIC of Lysozyme Chloride alone = 2.00 mg product/l
$MIC_B$ = MIC of BUSAN 77 ™ product alone = 2.00 mg product/l
[A] = MIC of Lysozyme Chloride in combination with BUSAN 77 ™ product (mg product/l)
[B] = MIC of BUSAN 77 ™ product in combination with Lysozyme Chloride (mg a.i./l)
*= A value <1 denotes synergistic activity of both components used simultaneously.

Example 6

Combinations of Lysozyme chloride (MP Biomedicals) with BUSAN 77™ product. The organism tested was *Phormidium faveolarum* (UTEX 427). The incubation period was 34 days at 24 C under 16 h of light and 8 h of darkness.

| Lysozyme [A] | BUSAN 77™ product [B] | $[A]/MIC_A$ | $[B]/MIC_B$ | $[A]/MIC_A$ + $[B]/MIC_B$ |
|---|---|---|---|---|
| 0 | 2 $MIC_B$ | 0.000 | 1.000 | 1.000 |
| 0.01 | 2 | 0.005 | 1.000 | 1.005 |
| 0.04 | 1 | 0.020 | 0.500 | 0.520* |
| 0.07 | 1 | 0.035 | 0.500 | 0.535 |
| 0.1 | 0.7 | 0.050 | 0.350 | 0.400 |
| 0.4 | 0.4 | 0.200 | 0.200 | 0.400 |
| 0.7 | 0.4 | 0.350 | 0.200 | 0.550 |
| 1 | 0.1 | 0.500 | 0.050 | 0.550 |
| 2 $MIC_A$ | 0 | 1.000 | 0.000 | 1.000 |

$MIC_A$ = MIC of Lysozyme Chloride alone = 2.00 mg product/l
$MIC_B$ = MIC of BUSAN 77 ™ product alone = 2.00 mg product/l
[A] = MIC of Lysozyme Chloride in combination with BUSAN 77 ™ product (mg product/l)
[B] = MIC of BUSAN 77 ™ product in combination with Lysozyme Chloride (mg a.i./l)
*= A value <1 denotes synergistic activity of both components used simultaneously.

Example 7

Combinations of Lysozyme Chloride (MP Biomedicals) with BUSAN 77™ product. The organism tested was *Staphylococcus aureus* (ATCC 6538). The incubation period was 18 hours at 37 C.

| Lysozyme [A] | BUSAN 77™ product [B] | $[A]/MIC_A$ | $[B]/MIC_B$ | $[A]/MIC_A$ + $[B]/MIC_B$ |
|---|---|---|---|---|
| 0 | 0.8 $MIC_B$ | 0.000 | 1.000 | 1.000 |
| 50 | 0.5 | 0.100 | 0.625 | 0.725* |
| 100 | 0.5 | 0.200 | 0.625 | 0.825* |
| 500 $MIC_A$ | 0 | 1.000 | 0.000 | 1.000 |

$MIC_A$ = MIC of Lysozyme Chloride alone = 500.0 mg product/l
$MIC_B$ = MIC of BUSAN 77 ™ product alone = 0.8 mg product/l
[A] = MIC of Lysozyme Chloride in combination with BUSAN 77 ™ product (mg product/l)
[B] = MIC of BUSAN 77 ™ product in combination with Lysozyme Chloride (mg product/l)
*= A value <1 denotes synergistic activity of both components used simultaneously.

Example 8

Combinations of Lysozyme chloride (MP Biomedicals) with BUSAN 77™ product. The organism tested was *Bacillus subtilis* (ATCC 6633). The incubation period was 18 hours at 37 C.

| Lysozyme [A] | BUSAN 77™ product [B] | $[A]/MIC_A$ | $[B]/MIC_B$ | $[A]/MIC_A$ + $[B]/MIC_B$ |
|---|---|---|---|---|
| 0 | 2 $MIC_B$ | 0.000 | 1.000 | 1.000 |
| 50 | 1 | 0.100 | 0.500 | 0.600* |
| 50 | 0.8 | 0.100 | 0.400 | 0.500* |
| 50 | 0.5 | 0.100 | 0.250 | 0.350* |
| 100 | 1 | 0.200 | 0.500 | 0.700* |
| 100 | 0.8 | 0.200 | 0.400 | 0.600* |

-continued

| Lysozyme [A] | BUSAN 77 ™ product [B] | [A]/MIC$_A$ | [B]/MIC$_B$ | [A]/MIC$_A$ + [B]/MIC$_B$ |
|---|---|---|---|---|
| 100 | 0.5 | 0.200 | 0.250 | 0.450* |
| 500 MIC$_A$ | 0 | 1.000 | 0.000 | 1.000 |

MIC$_A$ = MIC of Lysozyme Chloride alone = 500.0 mg product/l
MIC$_B$ = MIC of BUSAN 77 ™ product alone = 2.0 mg product/l
[A] = MIC of Lysozyme Chloride in combination with BUSAN 77 ™ product (mg product/l)
[B] = MIC of BUSAN 77 ™ product in combination with Lysozyme Chloride (mg product/l)
*= A value <1 denotes synergistic activity of both components used simultaneously.

Example 9

Combinations of Lysozyme chloride (MP Biomedicals) with BUSAN 77™ product. The organism tested was *Enterobacter aerogenes* (ATCC 13048). The incubation period was 18 hours at 37 C.

| Lysozyme [A] | BUSAN 77 ™ product [B] | [A]/MIC$_A$ | [B]/MIC$_B$ | [A]/MIC$_A$ + [B]/MIC$_B$ |
|---|---|---|---|---|
| 0 | 0.8 MIC$_B$ | 0.000 | 1.000 | 1.000 |
| 50 | 0.5 | 0.05 | 0.625 | 0.650* |
| 100 | 0.5 | 0.1 | 0.625 | 0.725* |
| 500 | 0.5 | 0.5 | 0.625 | 1.125 |
| >1000 MIC$_A$ | 0 | 1 | 0 | 1.000 |

MIC$_A$ = MIC of Lysozyme Chloride alone: >1000.0 mg product/l
Note:
The MIC of Lysozyme Chloride against *E. aerogenes* was not determined within the concentration range shown, however in order to demonstrate that synergism does exist, it was shown as greater than 1000 mg product/l which was the highest concentration tested.
MIC$_B$ = MIC of BUSAN 77 ™ product alone = 0.8 mg product/l
[A] = MIC of Lysozyme Chloride in combination with BUSAN 77 ™ product (mg product/l)
[B] = MIC of BUSAN 77 ™ product in combination with Lysozyme Chloride (mg product/l)
*= A value <1 denotes synergistic activity of both components used simultaneously.

Example 10

Combinations of Lysozyme chloride (NutriScience) with Sodium Chloride. The organism tested was *Chlorella* sp. (ATCC 7516). The incubation period was 14 days at 24 C under 16 h of light and 8 h of darkness.

| Lysozyme [A] | Sodium Chloride [B] | [A]/MIC$_A$ | [B]/MIC$_B$ | [A]/MIC$_A$ + [B]/MIC$_B$ |
|---|---|---|---|---|
| 0 | 30,000 MIC$_B$ | 0.000 | 1.000 | 1.000 |
| 0.1 | 30,000 | 0.050 | 1.000 | 1.050 |
| 0.4 | 30,000 | 0.200 | 1.000 | 1.200 |
| 0.7 | 6,000 | 0.350 | 0.200 | 0.550* |
| 1 | 6,000 | 0.500 | 0.200 | 0.700 |
| 2 MICA | 0 | 1.000 | 0.000 | 1.000 |

MIC$_A$ = MIC of Lysozyme Chloride alone = 2.00 mg product/l
MIC$_B$ = MIC of Sodium Chloride alone = 30,000 mg product/l
[A] = MIC of Lysozyme Chloride in combination with Sodium Chloride (mg product/l)
[B] = MIC of Sodium Chloride in combination with Lysozyme Chloride (mg a.i./l)
*= A value <1 denotes synergistic activity of both components used simultaneously.

Example 11

Combinations of Lysozyme chloride (NutriScience) with Sodium Chloride. The organism tested was *Phormidium faveolarum* (UTEX 427. The incubation period was 14 days at 24 C under 16 h of light and 8 h of darkness.

| Lysozyme [A] | Sodium Chloride [B] | [A]/MIC$_A$ | [B]/MIC$_B$ | [A]/MIC$_A$ + [B]/MIC$_B$ |
|---|---|---|---|---|
| 0 | 20,000 MIC$_B$ | 0.0 | 1.00 | 1.00 |
| 0.1 | 10,000 | 0.1 | 0.50 | 0.60* |
| 0.4 | 8,000 | 0.4 | 0.40 | 0.80 |
| 0.7 | 6,000 | 0.7 | 0.30 | 1.00 |
| 1 MIC$_A$ | 0 | 1.0 | 0.00 | 1.00 |

MIC$_A$ = MIC of Lysozyme Chloride alone = 2.00 mg product/l
MIC$_B$ = MIC of Sodium Chloride alone = 20,000 mg product/l
[A] = MIC of Lysozyme Chloride in combination with Sodium Chloride (mg product/l)
[B] = MIC of Sodium Chloride in combination with Lysozyme Chloride (mg a.i./l)
*= A value <1 denotes synergistic activity of both components used simultaneously.

Applicants specifically incorporate the entire contents of all cited references in this disclosure. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

Other embodiments of the present invention will be apparent to those skilled in the art from consideration of the present specification and practice of the present invention disclosed herein. It is intended that the present specification and examples be considered as exemplary only with a true scope and spirit of the invention being indicated by the following claims and equivalents thereof.

What is claimed is:

1. A method of controlling the growth of at least one microorganism in an aqueous system, the method comprising:
   providing a composition consisting essentially of lysozyme to the aqueous system, wherein said lysozyme is a heat-treated or thermally-modified lysozyme, or wherein said lysozyme is a lysozyme dimer.

2. The method of claim 1, wherein the method controls the growth of algae in the aqueous system.

3. The method of claim 1, wherein said lysozyme is a heat-treated or thermally-modified lysozyme.

4. The method of claim 1, wherein said lysozyme is a lysozyme dimer.

5. The method of claim 1, wherein the lysozyme is added to the aqueous system to provide a concentration of lysozyme of from about 0.01 to about 100 ppm.

6. The method of claim 1, wherein the lysozyme is added to the aqueous system to provide a concentration of lysozyme of from about 0.1 to about 10 ppm.

7. The method of claim 1, wherein the aqueous system is a swimming pool, hot tub or spa.

8. The method of claim 1 wherein the aqueous system is a re-circulated water system containing a chlorine generator and wherein the re-circulated water system contains about 2,000 to about 6,000 ppm of sodium chloride.

9. The method of claim 1, wherein the aqueous system is a medium for aquaculture.

10. The method of claim 1, wherein the aqueous system is a re-circulated water system from which chlorine has been removed.

11. A method of controlling the growth of at least one microorganism in an aqueous system, the method comprising:
providing a composition consisting essentially of a combination of at least one lysozyme and at least one quaternary ammonium compound, wherein said aqueous system is a medium for aquaculture, a re-circulated water system from which chlorine has been removed, a swimming pool, hot tub, spa, or a re-circulated water system containing a chlorine generator and wherein the re-circulated water system contains about 2,000 to about 6,000 ppm of sodium chloride, and wherein said lysozyme is a heat-treated or thermally-modified lysozyme, or wherein said lysozyme is a lysozyme dimer.

12. The method of claim 11, wherein the lysozyme is added to the aqueous system to provide a concentration of lysozyme of from about 0.01 to about 5,000 ppm.

13. The method of claim 11, wherein the lysozyme is added to the aqueous system to provide a concentration of lysozyme of from about 0.1 to about 500 ppm.

14. The method of claim 11, wherein the quaternary ammonium compound is added to the aqueous system to provide a concentration of the quaternary ammonium compound of from about 0.01 to about 1,000 ppm.

15. The method of claim 11, wherein the quaternary ammonium compound is added to the aqueous system to provide a concentration of the quaternary ammonium compound of from about 0.1 to about 100 ppm.

16. The method of claim 11, wherein the lysozyme and quaternary ammonium compound are added to the aqueous system to provide a concentration of lysozyme of from about 0.1 to about 500 ppm and a concentration of the quaternary ammonium compound of from about 0.1 to about 100 ppm.

17. The method of claim 11, wherein the method controls the growth of algae in an aqueous system.

18. A method of controlling the growth of at least one microorganism in an aqueous system, the method comprising:
providing a composition consisting essentially of lysozyme to the aqueous system, wherein said aqueous system is a medium for aquaculture, a re-circulated water system from which chlorine has been removed, a swimming pool, hot tub, spa, or a re-circulated water system containing a chlorine generator and wherein the re-circulated water system contains about 2,000 to about 6,000 ppm of sodium chloride, and wherein said lysozyme is a heat-treated or thermally-modified lysozyme, or wherein said lysozyme is a lysozyme dimer.

19. The method of claim 18, wherein the lysozyme is added to the aqueous system to provide a concentration of lysozyme of from about 0.01 to about 100 ppm.

20. The method of claim 18, wherein the lysozyme is added to the aqueous system to provide a concentration of lysozyme of from about 0.1 to about 10 ppm.

21. A method of controlling the growth of at least one microorganism in an aqueous system, the method comprising:
providing a composition consisting of lysozyme to the aqueous system.

* * * * *